(12) United States Patent
Pirotte

(10) Patent No.: US 10,582,706 B2
(45) Date of Patent: *Mar. 10, 2020

(54) AQUEOUS SUSPENSION CONCENTRATE COMPRISING AN ACID SALT OF DODECYLGUANIDINE

(76) Inventor: Alan Pirotte, Houffalize (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/239,513

(22) PCT Filed: Aug. 22, 2012

(86) PCT No.: PCT/EP2012/066362
§ 371 (c)(1),
(2), (4) Date: Feb. 18, 2014

(87) PCT Pub. No.: WO2013/026889
PCT Pub. Date: Feb. 28, 2013

(65) Prior Publication Data
US 2014/0193503 A1 Jul. 10, 2014

(30) Foreign Application Priority Data
Aug. 22, 2011 (WO) ............. PCT/EP2011/064397

(51) Int. Cl.
*A01N 25/04* (2006.01)
*A01N 43/80* (2006.01)
*A01N 47/44* (2006.01)

(52) U.S. Cl.
CPC ............ *A01N 25/04* (2013.01); *A01N 43/80* (2013.01); *A01N 47/44* (2013.01)

(58) Field of Classification Search
None
See application file for complete search history.

(56) References Cited

U.S. PATENT DOCUMENTS

| 3,312,589 A | 4/1967 | Entley et al. |
| 4,502,861 A | 3/1985 | Becker et al. |

(Continued)

FOREIGN PATENT DOCUMENTS

| DE | 3248115 A1 | 6/1984 |
| EP | 0007731 | 2/1980 |

(Continued)

OTHER PUBLICATIONS

OECD, "OECD Draft Guidance Document for Storage Stability Testing of Plant Protection and Biocidal Products", Jan. 6, 2015. (Year: 2015).*

(Continued)

*Primary Examiner* — Jianfeng Song
(74) *Attorney, Agent, or Firm* — Carmody Torrance Sandak & Hennessey LLP

(57) ABSTRACT

The invention concerns a suspension concentrate comprising, expressed by weight based on the total weight of the composition: a) 40 to 80% particles of dodecylguanidine or an acid salt of dodecylguanidine of the structure (1), wherein X represents an acid residue of a monocarboxylic, dicarboxylic or a mineral acid, b) 0 to 10% of an anti-freeze compound, c) 1 to 10% of a wetting agent and/or d) a dispersing agent, e) 0 to 5% of an antifoaming agent, f) remainder water characterized in that, the median diameter of the particles ($d_{50}$) is at least 7 μm and below 40 μm; and its use for the treatment of a fungicidal disease on crops or ornamental plants.

(Continued)

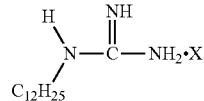

(1)

2 Claims, 4 Drawing Sheets

(56) References Cited

U.S. PATENT DOCUMENTS

| | | | | |
|---|---|---|---|---|
| 5,372,989 | A * | 12/1994 | Geigle | A01N 25/14 424/409 |
| 5,976,600 | A * | 11/1999 | Ruszkay | A23G 1/40 426/506 |
| 6,096,769 | A * | 8/2000 | Perlitz | A01N 43/653 514/361 |
| 6,462,052 | B1 | 10/2002 | Duvert et al. | |
| 6,517,853 | B1 * | 2/2003 | George | A61K 9/10 424/405 |
| 6,559,156 | B1 * | 5/2003 | Dimitrova | A01N 43/54 514/275 |
| 2006/0166898 | A1 * | 7/2006 | Chen | A01N 25/04 514/22 |
| 2008/0182755 | A1 | 7/2008 | Kozuki | |
| 2008/0274154 | A1 | 11/2008 | Bussmann et al. | |
| 2009/0325808 | A1 | 12/2009 | Stern et al. | |
| 2011/0033436 | A1 * | 2/2011 | Chen | A01N 63/00 424/93.461 |
| 2014/0148510 | A1 | 5/2014 | Pirotte | |
| 2014/0193503 | A1 | 7/2014 | Pirotte | |

FOREIGN PATENT DOCUMENTS

| | | |
|---|---|---|
| EP | 0388239 | 9/1990 |
| EP | 1625791 A1 | 2/2006 |
| FR | 2582546 A2 | 12/1986 |
| WO | WO 2006/002984 A1 | 1/2006 |
| WO | WO 2007/017501 A2 | 2/2007 |
| WO | WO 2007/110355 A2 | 10/2007 |
| WO | WO 2009/082939 A1 | 7/2009 |
| WO | WO-2009082939 * | 7/2009 |

OTHER PUBLICATIONS

International Search Report and Written Opinion of the International Searching Authority for International Application No. PCT/EP2012/066362, dated Oct. 30, 2012.

Extended European Search Report for European Patent Application No. 12181421.4, dated Oct. 30, 2012.

"Material Safety Data Sheet, Equal 65 WP (Dodine 65 WP)," Norac Concepts Inc, pp. 1-3 (Nov. 19, 2007). Retrieved from the Internet: URL:http://www.bartlett.ca/Bartlett/nmb/MSDSLabel.nsf/33679510e3c80d96852574a20055f364/0cge5ecdd7d4490385256bba006a99b3/$FILE/Equal 65WP msds english.pdf [retrieved on Sep. 21, 2011].

"Fiche de Donnees de Securite," Solvesso 200, ExxonMobil, pp. 1-5 (Apr. 4, 2012).

"Pluronic® PE types," Technical Information, BASF The Chemical Company, pp. 1-16 (Mar. 2005).

Dodine, "The pesticide manual ED—Worthing C R, Hance R J", Pesticide Manual. World Compendium; [Pesticide Manual], Farnham, BCPC, GB, pp. 382-383 (Jan. 1, 1995).

Pfannkoch, E. "The Preparation of Buffers and Other Solutions: A Chemist's Perspective." Molecular Biology Problem Solver: A Laboratory Guide. (c) 2001. Edited by Alan S. Gerstein.

Somers, E., et al. "Effect of Dodine Acetate on the Electrophoretic Mobility of Neurospora crassa Conidia." J. gen. Microbiol. (1967), vol. 48, pp. 147-154.

* cited by examiner

AQUEOUS SUSPENSION CONCENTRATE COMPRISING AN ACID SALT OF DODECYLGUANIDINE

CROSS-REFERENCE TO RELATED APPLICATIONS

This application is the U.S. National Phase under 35 U.S.C. § 371 of International Application PCT/EP2012/066362, filed Aug. 22, 2012, which claims priority to PCT/EP2011/064397, filed Aug. 22, 2011.

TECHNICAL FIELD

The invention pertains to the technical field of formulations of active ingredients for application in crop protection. In particular, the invention pertains to an aqueous suspension concentrate comprising dodecylguanidine, in particular dodecylguanidine acetate, commonly known as dodine. The invention also relates to uses of the composition in agriculture.

BACKGROUND

Crop protection compositions can in principle be formulated in different ways, the properties of the active ingredients and the nature of the formulation possibly posing problems in terms of the ease of preparation, stability, ease of application, and activity of the formulations. Moreover, for reasons of economics and ecology, certain formulations are more advantageous than others.

Generally there is a need for highly concentrated formulations of active ingredients, since such formulations are associated with a number of advantages. For example, the cost and complexity of packaging required is less than for low-concentration formulations. Correspondingly there is a resultant reduction in the cost and complexity of production, transport, and storage, and additionally the operations of preparing the spray liquids that are used in agriculture, for example, are simplified as a result of the handling of low-volume containers of crop protection compositions, such as during the operations of dispensing and of stir-mixing, for example.

Liquid formulations have the advantage over powder formulations that upon the reconstitution of a spray liquid, typically by adding water, they do not produce dust. Preferred liquid formulations, at they are concentrated, are suspension concentrates. A suspension concentrate is defined as a suspension of solid particulate active ingredients in a liquid intended for dilution with water before use. In spite of their ease of use, they are not as concentrated as e.g. powders. The amount of liquid phase comprised in the formulation, such oil or water, is typically more than half.

Product development has targeted to obtain fungicidal suspension concentrates comprising as much active ingredient as possible. However, the degree of concentration is limited by the requirement to obtain a stable product, that is wherein the solid particulates do not settle and which can be stored over extended periods of time.

Efforts have concentrated on the reduction of the particle size of the active ingredient. An increased surface area obtained thereby is often correlated with a higher chemical activity. Formulators have introduced surfactants into suspension concentrates to improve wetting properties to keep the active ingredient particles dispersed in the liquid phase.

Dodecylguanidine acetate, known as dodine, is a fungicide recommended for the control of a number of major fungal diseases of crops. Dodine is currently formulated as wettable powders, suspension concentrates and wettable granules. It is a slightly yellow fine powder with low solubility in water, in particular 0.63 g/l at 25° C., and organic solvents. It is used against almond scab; apple and pear scab; banana sigatoka; cherry leaf spot; olive leaf spot; peach bacterial spot and leaf curl; peanut early and late leaf spot; pecan scab, liver spot, brown and downy leaf spot, leaf blotch and downy mildew; and walnut anthracnose.

In spite of the importance of these active ingredients, developments in the area of suspension concentrates comprising dodecylguanidine, or a salt, or ester thereof, have been limited. Stable suspension concentrates of dodecylguanidine acetate typically comprise 400 g active ingredient per liter. This is disadvantageous as transport of products is costly. This is certainly the case where most of the product is water. In order to reduce the environmental impact of such formulation it would be advantageous to be able to produce formulations that are much more concentrated. It is also of interest to have formulations that have an improved toxicological profile, yet are sufficiently effective against the targeted pest.

US 2008/274154 teaches that suspension concentrates containing acrylic graft copolymer surfactant and an ionic alkoxylated polyarylphenol phosphate ester surfactant are stable over time at high concentrations of active materials.

US 2009/325808 describes highly concentrated suspension of slightly water soluble pesticides that are protected from Ostwald ripening by the use of polymeric surfactants. Also EP 0 007 731 discloses that highly concentrated suspensions of agrochemical active ingredients may be obtained using polymeric surfactants.

WO 2009/082939 describes that very concentrated suspensions of fungicides may be obtained by stabilizing an agrochemical active ingredient with one non-ionic dispersing agent and one anionic dispersing agent. Dodine is one of the fungicides that can be formulated in this way.

The above mentioned disclosures relate to anionic surfactants. This type of surfactant is not compatible with dodine.

EP 0 388 239 discloses the use of so-called structured surfactants for the preparation of highly concentrated suspensions of agrochemical or biocidal active ingredients.

None of these disclosures describes suspension concentrates of dodecylguanidine, or its salts, having a concentration above 40%.

There remains a need in the art for improved fungicidal suspension concentrates comprising dodecyl guanidine, or a salt, or ester thereof.

The present invention aims to resolve at least some of the problems mentioned above. The invention thereto aims to provide a more concentrated formulation than could be achieved thus far. The fungicidal suspension concentrate should be stable upon prolonged periods of storage. It should be economical. The ecological profile should be considered. The efficacy for the treatment of fungicidal diseases on agricultural crops should be maintained or improved.

SUMMARY OF THE INVENTION

The present invention provides an aqueous suspension concentrate, as presented by claim 1, comprising active ingredient in the form of particles, characterized in that the median diameter of the particles ($d_{50}$) is at least 7 µm and below 40 µm.

By the term "aqueous" as used herein, is meant that the solvent used in the composition is mainly water. Hence, "aqueous" and "water-based" may be considered synonyms. Water-based formulations generally have the advantage that they require little or no organic solvent fraction.

By the term "active" as used herein, is meant an ingredient that is chemically active and/or biologically active in origin. By the term "active ingredient" as used herein, is meant dodecylguanidine or a salt, or ester thereof. In this regard an "active" ingredient can be a single ingredient or a combination of ingredients; and the meaning of the term "active" shall be understood to include but not be limited to dodecylguanidine or a salt, or ester thereof.

Particle size is typically defined as a log-normal distribution with a median diameter or $d_{50}$—that is 50% of the particles measured are less than the median value and 50% are greater than the median value. The term "particle size distribution" as used herein refers to the relative percentages by weight or volume of each of the different size fractions of a particulate matter. The term "median particle size", "median diameter of particles", "$d_{50}$", as used herein refers to the median or 50% quantile of a particle size distribution. The term "$d_{50}$" hence defines a size where 50 volume percent of the particles have sizes less than the value given.

The particle size distributions for the present application can be measured using laser light diffraction equipment, such as are sold by Malvern Instruments Ltd., Malvern, Worcestershire, United Kingdom. Other types of equipment are also suitable for particle size distribution determinations.

Suspension concentrates of dodecylguanidine or a salt, or ester thereof, as known to a person skilled in the art, typically have a median particle diameter below 5 μm, typically around 3 μm.

The inventors have found to their surprise that the increase of the median particle diameter, allowed the preparation of highly concentrated suspension concentrates. These provide an economical advantage as savings can be made on transportation costs. The compositions provided by the invention are stable over prolonged periods of time and are easy-to-use.

In a second aspect, the present invention provides the use of a composition according to an embodiment of the invention for the treatment of a fungicidal disease on crops or ornamental plants.

By the term "fungicidal disease" as used herein, is meant a disease caused by a fungus. By the term "fungicide" as used herein, is meant any toxin used to kill or inhibit growth of fungi. The present invention in particular relates to fungicides targeting fungi that cause economic damage to crops or ornamental plants.

Particularly targeted "fungicidal diseases" in the present invention are almond scab; apple and pear scab; banana sigatoka; cherry leaf spot; peach bacterial spot and leaf curl; olive leaf spot; peanut early and late leaf spot; pecan scab, liver spot, brown and downy leaf spot, leaf blotch and downy mildew; and walnut anthracnose.

By the term "crops" or "crop plants" as used herein, is meant any kind of agricultural crop, including but not limited to cereals, rice, legumes, cotton, tobacco, vegetables and fruit plants. Preferred are high value crops like fruit plants, ornamental crops and nuts.

Fruit plants include, for example, fruits from the Rosacea family, like apple, pear, and quince; stone fruits, like apricot, cherry, plum and peach; berries, specifically bramble fruits, like blackberry, raspberry, loganberry and thimbleberry, true berries, like blueberry and cranberry, other berries, like gooseberry and mulberry; accessory fruits, like strawberry; fruits from the Cucurbitacea family, like gourds, including squash and pumpkin; melons and watermelons; citrus and other subtropical fruits, like lemon, lime, grapefruit, mandarine, clementine, tangerine, orange, avocado, guave, kumquat, logan, lychee and passion fruit; dates, figs, grapes, olives and pomegranate; and tropical fruits, like banana, coconut, durian, eggfruit, mango, mangosteen, papaya, pineapple and tamarind.

Preferred fruit plants are apple, banana, cherry, olive, peach and pear.

Ornamental crops include, but are not limited to, aster, azalea, begonia, boxwood, cacti, caladium, calla, calendula, carnation, chrysanthemum, coleus, columbine, dahlia, daisy, daylily, delphinium, dianthus, Easter lily, fern, ficus, foxglove, fuchsia, gardenia, geranium, gerbera, gladioli, hibiscus, impatiens, iris, ivy, marigold, nasturtium, pansy, peony, petunia, phlox, pinks, poinsettia, rosemary, rose, rubberplant, salvia, sedum, snapdragon, verbena, vinca, wandering jew and zinnia.

Preferred ornamental crops are fern and rose.

Nuts include almond, Brazil nut, butternut, cashew, chestnut, macadamia, pecan, peanut, pistachio and walnut. Preferred nuts are almond, peanut, pecan nut and walnut.

Compositions provided by the invention are at least as effective as prior art compositions when used in comparable dose rates per hectare. In particular, the efficacy of compositions provided by the invention for the treatment of fungicidal diseases on agricultural crops, particularly apple scab, is maintained or improved compared to suspension concentrates comprising 400 g/l of dodecylguanidine or a salt, or ester thereof. This was unexpected as it was believed that efficacy would decrease with an increased particle size, due to a decreased surface contact.

DETAILED DESCRIPTION OF THE INVENTION

Figure 1:
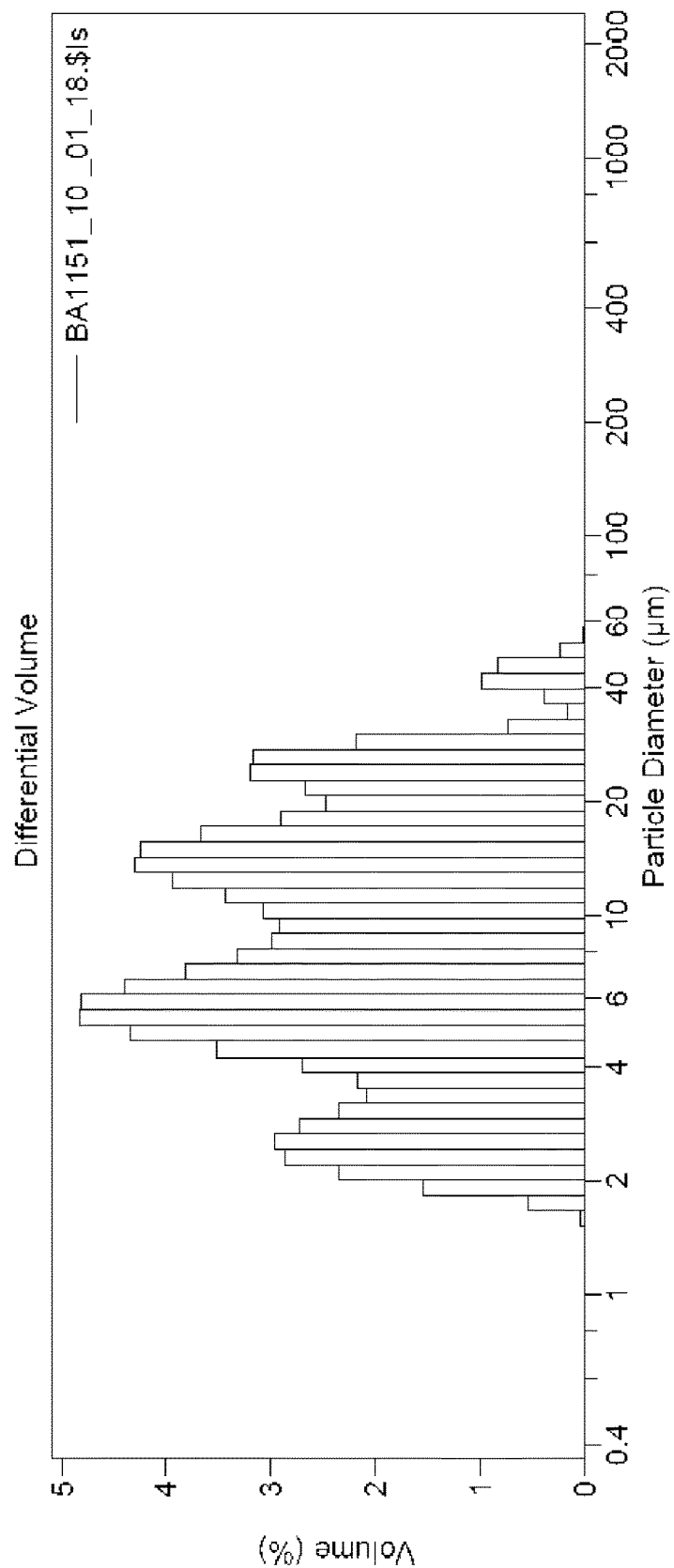
FIG. 1 depicts a typical particle size distribution of a Dodine 544 g/l SC solution according to an embodiment of the invention.

The present invention concerns an improved aqueous suspension concentrate, and uses of the suspension concentrate.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

In a first aspect, the invention provides an aqueous suspension concentrate with a composition comprising, expressed by weight based on the total weight of the composition:
  a) 40 to 80%, preferably 40 to 70%, particles of dodecylguanidine, a salt or ester thereof;
  b) 0 to 10% of an anti-freeze compound,
  c) 1 to 10% of a wetting agent and/or d) a dispersing agent,
  e) 0 to 5% of an antifoaming agent,
  f) remainder water
characterized in that, the median diameter of the particles ($d_{50}$) is at least 7 μm and below 40 μm.

The upper limit of 40 μm is dictated by a spray nozzle as there is a risk of blocking them when too many particles over 40 μm are present. Between 7 μm and 40 μm the suspension concentrate has an improved viscosity, below 1500 cPS, which is more workable and allows an increase in the active ingredient content of the formulation.

In a preferred embodiment, $d_{50}$ is below 20 μm. Preferably $d_{50}$ is 7-20 μm, more preferably $d_{50}$ is 7-15 μm, most preferably $d_{50}$ is 7-10 μm. Within this range the SC-formulation, even if highly concentrated, remains stable upon prolonged storage.

The term "aqueous suspension concentrate" refers to suspension concentrates based on water.

The expression "% by weight" (weight percent), here and throughout the description unless otherwise defined, refers to the relative weight of the respective component based on the overall weight of the formulation.

The fraction of water in the suspension concentrates of the invention may be in general 20%-60% by weight, preferably 30%-45% by weight, more preferably 35%-40% by weight.

The fraction of active ingredients (component a) in the suspension concentrates of the invention is preferably 40%-80% by weight, in particular 45%-60% by weight, more preferably 50%-55% by weight.

In a preferred embodiment of the invention the active ingredients (component a) are present with a minimum content of 400 g of active ingredient/l, preferably 440-820 g of active ingredient/l, more preferably 544 g/l of active ingredient/l of the overall formulation.

Suitable active ingredients for use in the invention are dodecylguanidine or a salt, or ester thereof; or mixtures thereof.

By the term "dodecylguanidine, a salt or ester thereof" an acid salt of dodecylguanidine of the structure (1) is meant,

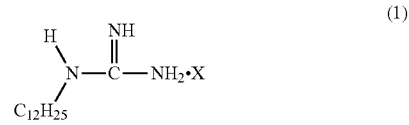

wherein X represents an acid residue of a monocarboxylic acid such as acetic, propionic, capric, stearic, benzoic, and naphtoic; dicarboxylic acid such as malonic or succinic and a mineral acid such as hydrochloric, sulphuric, bisulphuric or nitric acid.

In particularly preferred embodiment of the invention, the dodecylguanidine compound is an acetate of dodecylguanidine, commonly known as dodine.

In an especially preferred embodiment, the fungicidal suspension concentrate comprises dodine as active ingredient, preferably in a concentration of 544 g/l.

Dodine, 1-dodecylguanidinium acetate (dodecylguanidine monoacetate), is a fungicide and bactericide registered for foliar use on pome fruits, stone fruits including cherries, and nuts including walnuts.

Suspension concentrates of the invention are characterized in that 50% of the particles of the overall formulation, preferably 50% of the particles of the active ingredients (component a), have a size of at least 7 μm (d50>=7 μm).

More preferably 60%, even more preferably 80%, most preferably more than 90%, of the particles of the overall suspension concentrate have a size of at least 7 μm.

In a preferred embodiment at most 2% of the particles have a particle size of at least 75 μm ($d_{98}$).

It is additionally possible to add further formulation assistants to these formulations, such as anti-freeze compounds, wetting agents, dispersing agents, antifoaming agents, preservatives, or dyes.

These formulation assistants are described for example in *Chemistry and Technology of Agrochemical Formulations*, ed. D. A. Knowles, Kluwer Academic Publishers (1998) and *Controlled-Release Delivery Systems for Pesticides*, Herbert B. Scher, Marcel Dekker, Inc. (1999).

The fraction of these formulation assistants in the suspension concentrates of the invention is preferably 0%-30% by weight, in particular 2%-15% by weight, more preferably 5%-10% by weight.

In a preferred embodiment of the invention, the anti-freeze compound (component b) is selected from the list of glycols, glycerols, urea and mixtures thereof.

In a preferred embodiment, the anti-freeze compound (component b) is a glycol selected from the list of ethylene glycol, diethylene glycol, triethylene glycol, propylene glycol, dipropylene glycol, tripropyleneglycol, glycerol, and mixtures thereof.

In a particularly preferred embodiment, the anti-freeze compound is propylene glycol.

The term "surfactant"—which includes the terms "emulsifier" and "detergent"—as used herein means a composition of matter that either alters surface tension when dissolved in water or an aqueous solution or alters interfacial tension between immiscible liquids or a liquid and a solid.

Surfactants suitable for purposes of the present invention are listed in McCutcheon's Emulsifiers & Detergents, at pages 287-310 of the North American Edition (1994), and in McCutcheon's Emulsifiers & Detergents, at pages 257-278 and 280 of the International Edition (1994), both published by MC Publishing Co. (McCutcheon Division) of Glen Rock, N.J.

In this regard, suitable surfactants include, but are not limited to, alkylamine ethoxylates, acrylate graft copolymer ethoxylates, block polymers, carboxylated alcohol or alkylphenol ethoxylates, alcohol ethoxylates, ethoxylated alkylphenols, glycol esters, polyethylene glycols, silicone-based surfactants, and tristyrylphenol ethoxylates.

In a preferred embodiment, the surfactant is an acrylate graft copolymer. An example of an acrylate graft copolymer is Tersperse 2500 (Huntsman). This surfactant acts is easily soluble in water and acts as a dispersant.

Preferred surfactants are selected from the group consisting of wetting agents, dispersing agents and mixtures thereof.

In a preferred embodiment the wetting/dispersing agent is not an anionic wetting or dispersing agent as this may be incompatible with dodine. In a more preferred embodiment, the dispersing/wetting agent is non-ionic.

Wetting agents serve to reduce the surface tension at the water-solid interface and therefore increase the tendency of the water to contact the complete surface of the active ingredient particles.

In a preferred embodiment of the invention, the wetting agent (component c) is an ethoxylate. In a particularly preferred embodiment of the invention, the wetting agent (component c) is selected from the list of alkylamine ethoxylates, alkylphenol ethoxylates, alcohol ethoxylates, and tristyrylphenol ethoxylates.

In a preferred embodiment the wetting agent (component c) is an alkylamine ethoxylate. Examples of alkylamine ethoxylate wetting agents (component c) are Rhodameen RAM 7 (Rhodia) or Emulson AG/NHT (Cesalpina). The advantage of this surfactant is that it acts as an emulsifier and shows a high compatibility degree with dodine.

In another preferred embodiment the wetting agent (component c) is an alcohol ethoxylate. Alcohol ethoxylates are prepared from saturated or unsaturated, linear or branched aliphatic alcohols having on average from 8 to 20 carbon atoms, and which contain from 5 to 25, typically from 10 to 20, ethylene oxide units per molecule. Preferred are alcohol ethoxylates which contain from 12 to 18 carbon atoms in the alcohol moiety and 10 to 20 ethylene oxide units.

Examples of alcohol ethoxylates are Brij, Volpo, Arlasolve, Atphos, Synperonic and Lubrol, Synperonic 91-6, Atplus MBA 11-7 (Uniqema).

Examples of tristyrylphenol ethoxylate wetting agents (component c) are Soprophor® 3D33 (=tristyrylphenol ethoxylated with 16 EO and phosphated), Soprophor® BSU (=tristyrylphenol ethoxylated with 16 EO), Soprophor® CY/8 (Rhodia) (=tristyrylphenol ethoxylated with 20 EO), and Hoe® S3474 (=tristyrylphenol ethoxylated with 20 EO) and in the form of the Sapogenat® T product (Clariant), such as Sapogenate T 100 (=triisobutylphenol ethoxylated with 10 EO), for example.

The fraction of surfactants in the suspension concentrates of the invention is generally 0%-10% by weight, preferably 1%-5% by weight, more preferably 2%-4% by weight, most preferably around 3% by weight.

In a preferred embodiment of the invention, the ratio of wetting agent to particles of dodecylguanidine or a salt, or ester thereof, is between 1/8 to 1/80, preferably between 1/10 to 1/25, more preferably between 0.04-0.06.

The term "dispersant" or "dispersing agent" as used herein connotes a surface-active agent that is added to suspending media to promote uniform suspension or separation of solid particles, often of micrometer size.

Dispersants (components d) suitable for purposes of the present invention are listed in McCutcheon's Functional Materials, at pages 122-142 of the North American Edition (1994), as well as in McCutcheon's Functional Materials, at pages 47-56 of the International Edition (1994), both published by MC Publishing Company (McCutcheon Division) of Glen Rock, N.J.

In this regard, suitable dispersants include, but are not limited to, acrylate graft copolymers. Examples of acrylate graft copolymer dispersing agents (component d) are Tersperse 2500 (Huntsman).

The term "antifoaming agent" or "foam-control" agent or ingredient shall be understood to mean a substance that is used to reduce foaming. Foaming may result from the presence of foam-inducing agents as proteins, gases, or nitrogenous materials. The presence of foam is generally undesirable because foam may interfere with processing.

Antifoaming agents are generally discussed at pages 430-447 in the Kirk-Othmer Encyclopedia of Chemical Technology, third edition, volume 7, published 1979 by John Wiley & Sons, Inc.

Suitable antifoaming agents (component e) for purposes of the present invention include but are not limited to silicone-based defoamers, from Wacker, Rhodia or Dow Corning, for example; acetylene-based defoamers, such as those from Air Products, for example, and perfluoroalkylphosphinic acid and phosphonic acids and their salts.

Preferred defoamers are those from the group of linear polydimethylsiloxanes having an average dynamic viscosity, measured at 25° C., in the range from 1000 to 800 mPa·s, usually 1200 to 6000 mPa·s, and containing silica. Silica includes polysilicic acids, meta-silicic acid, ortho-silicic acid, silica gel, silicic acid gels, kieselguhr, precipitated SiO2, and the like.

Defoamers from the group of linear polydimethylsiloxanes contain as their chemical backbone a compound of the formula HO—[Si(CH3)2-O-]n-H, in which the end groups are modified, by etherification for example, or are attached to the groups —Si(CH3)3. Examples of defoamers of this kind are Rhodorsil® Antifoam 416. Other suitable defoamers are Rhodorsil® 1824, Antimussol 4459-2 (Clariant, Defoamer V4459 (Clariant), SE Visk and AS EM SE 39 (Wacker).

Particularly preferred are polydimethylsiloxane, wherein two methyl groups are attached to each silicon atom to form $(H_3C)[SiO(CH_3)_2]_nSi(CH_3)$ and simethicone, which is a mixture of polydimethylsiloxane and silica.

An example of a suitable defoamer is Rhodorsil® 481 and Rhodorsil® 454 (polydimethylsiloxane and silicon) from Rhodia.

An aqueous suspension concentrate according to an embodiment of the invention may further comprise g) a thickening agent and/or h) a biocidal compound.

A suitable thickening agent (component g) is a hydroxyethylcellulose, a gelling and thickening agent derived from cellulose. Especially preferred is hydroxyethylcellulose surface-treated with glyoxal. A suitable thickener is, for example Natrosol® 250 HXR from Hercules-Aqualon.

Suitable preservatives (component h) are typical biocidal compounds, an example being Promex Na20S (1,2-Benzisothiazolin-3-one) from Prom Chem, and Acticide® MBS (mixture of 1,2-benzoisothiazol-3(2H)-one and 2-methyl-2H-isothiazol-3-one, biocide) from Thor.

In a preferred embodiment of the invention, the suspension concentrate further comprises g) a thickening agent and/or h) a biocidal compound in a concentration of up to 1%, expressed by weight based on the total weight of the composition.

In one preferred embodiment of the invention grinding continues until 50% of the particles of the active ingredient, technical grade, have a size of at least 8 µm (d50≥8 µm), preferably at least 10 µm, more preferably at least 11 µm.

Preferably in this case at least 60% of the particles of the active ingredients (component a) in the formulation have a particle size of d50 of at least 7 µm, more preferably 70%, most preferably 80% of the active ingredient particles have a particle size of at least 7 µm.

In an embodiment of the invention, the median diameter of the particles of the active ingredient is at least 10 µm, preferably at least 12 µm, more preferably at least 14 µm, most preferably around 15 µm.

In a preferred embodiment of the invention the viscosity of the suspension concentrate is between 500 and 1.000 mPa·s (cps), preferably between 600 and 900 mPa·s (cps), more preferably between 700 and 800 mPa·s (cps), most preferably around 750 mPa·s (cps).

Viscosity measurement systems are known to a person skilled in the art. For instance, viscosity can be measured using a Brookfield system with a spindle 2 at 20 rpm and temperature of 20° C.

In a preferred embodiment of the invention, the suspension concentrate is comprising, expressed by weight based on the total weight of the composition:
a) 45 to 60% of particles of dodecylguanidine or a salt, or ester thereof;
b) 1 to 5% of an anti-freeze compound,
c) 1 to 5% of a wetting agent,
d) up to 2% of a dispersing agent,
e) up to 2% of an antifoaming agent, and
f) remainder water.

In a preferred embodiment of the invention, the suspension concentrate comprises, expressed by weight based on the total weight of the composition:
a) 50 to 55% of particles of dodecylguanidine or a salt, or ester thereof;
b) 3% of an anti-freeze compound,
c) 3% of a wetting agent,
d) 1% of a dispersing agent,
e) 1% of an antifoaming agent,
g) 0.1% of a thickener,
h) 0.1% of a biocide, and
f) remainder water.

With the suspension concentrates of the invention it is generally possible to achieve an equal or better biological effect for the same application rate. Due to the larger particle size versus conventional formulations, the formulation may be less toxic to humans.

Besides this the high-concentration formulation of active ingredients in the suspension concentrates of the invention permits the associated advantages, such as a lower level of packaging, as a result of which the cost and complexity involved in producing, transporting, and storing is simplified and the preparation of the spray liquors used in agriculture can be managed more effectively as a result of the smaller quantities, such as in the context of dispensing operations and stir-mixing operations, for example.

The suspension concentrates of the invention additionally surprisingly display outstanding dispersing and stabilizing properties following further dilution with liquids, preferably water.

Additionally the suspension concentrates of the invention produce formulations which are stable on storage (for long periods).

The invention further provides compositions obtainable from the suspension concentrate of the invention by dilution with liquids, preferably aqueous liquids, more preferably water.

It can be advantageous to add further active ingredients to the compositions thus obtained, preferably active agrochemical ingredients (e.g., as tank mix partners in the form of corresponding formulations) and/or auxiliaries and additives customary for the application, examples being self-emulsifying oils such as vegetable oils or liquid paraffins and/or fertilizers. The present invention accordingly further provides compositions of this kind, preferably fungicidal compositions, which are based on the suspension concentrates of the invention.

In a third aspect, the invention provides uses of a suspension concentrate according to an embodiment of the invention for the treatment of a fungicidal disease on agricultural crops.

In a preferred embodiment, a suspension concentrate according to an embodiment of the invention is used for the treatment of scab on apples.

Apple scab, caused by the fungal pathogen *Venturia inaequalis*, is considered to be the most important single disease of apple worldwide and one of the most costly to control.

In efficacy trial the treatment of apple scab with Dodine 544 SC was compared with Syllit® 400 SC, a commercially available product comprising 400 g/l dodine, and for several crops Dodine 544 SC was substantially more efficient than Syllit® 400 SC.

In a fourth aspect, the invention provides a method for the treatment of an agricultural crop, comprising the step of diluting an aqueous suspension concentrate according to an embodiment of the invention, and applying to the agricultural crop an effective amount of the diluted aqueous suspension concentrate.

By the term "effective amount" as used herein it is meant the least amount of the active ingredient that is required to control the fungal disease concerned.

In a preferred embodiment, about 1.25 litres of an aqueous suspension concentrate according to the invention is dissolved in 400 litres of water to prepare a composition for the treatment of 1 ha.

In spite of the increased particle size of the active ingredient, believed to be detrimental for the biological activity of the spray liquid, a composition according to the invention, in particular dodine 544 SC (suspension concentrate comprising 544 g/l dodine), was at least equally effective as Syllit® 400 SC (suspension concentrate comprising 400 g/l dodine).

The suspension concentrates of the invention are produced in a known way (see Winnacker-Küchler, "Chemische Technologie", volume 7, C. Hanser Verlag Munich, $4^{th}$ ed. 1986), such as by wet grinding of the components, for example, which can take place in appropriate mills, such as in bead mills, for example (such as batch bead mills, for example, from Drais for example, or continuous bead mills, from Bachofen, for example), or in colloid mills (such as toothed colloid mills, from Probst+Claasen, for example).

Suspension concentrates described in the art are typically prepared by wet grinding. By the term "wet grinding" is meant in the present invention the milling of materials in water or other liquid.

The active ingredient in particle form is typically wet grinded until the active ingredient reaches a particle size having a median diameter or $d_{50}$ of about 3 μm. The formulation then has a viscosity of around 1000 mPa·s (cps).

Unexpectedly, the suspension concentrates containing particles of an abnormally high particle size compared to suspension concentrates known in the art of dodecylguanidine, were stable over prolonged periods of time.

In a preferred embodiment, a suspension concentrate according to an embodiment of the invention will be stable upon storage at a temperature of 25° C. for a period of at least 6 months, preferably 12 months, more preferably 18 months, most preferably at least 24 months. In a preferred embodiment, a suspension concentrate of the invention has a storage stability, of at least one year. The storage stability can be measured by techniques known to a person skilled in the art.

To obtain a fast indication of the prolonged storage stability of a product CIPAC method MT 46 accelerated storage test by heating can be used. Several parameters before and after heating are typically analyzed and compared to determine if the products has changed: pH (CIPAC MT 75.3), pourability (CIPAC MT 148.1), suspensibility (CIPAC MT 184), spontaneity of dispersion (CIPAC MT 160), wet sieve test (CIPAC MT 185), persistent foam (CIPAC MT 47.2), particle size distribution (CIPAC MT 187), low temperature stability (CIPAC MT 39.3).

A good product pourability demonstrates that the user can make use of the maximum amount of the preparation and that an excessive amount of the material does not remain in the container. A suspension concentrate of good pourability has max. 5% residue and max. 0.25% rinsed residue. In a preferred embodiment, the suspension concentrate has a pour residue below 4% and a rinsed residue below 0.5% as measured after storage for 14 days at 54° C.+/−2° C. according to CIPAC MT 46.3.1.

In a wet sieve test the residue remaining on a sieve is determined after dispersion to ensure no unacceptable residue remains which causes the blockage of nozzles or filters on application equipment. Good product performance is characterized by a maximum of 2% retained on a 75 μm sieve.

Active ingredient content may be measured by analytical methods known to a person skilled in the art. Dodine content, for instance may be determined by a reversed-phase HPLC using a 250×4.6 mm ODS-2 column, (e.g. Inertsil 5ODS-2, 5 μm particle size, or equivalent) with mobile phase composed of acetonitrile and water with 0.005M heptane sulfonic acid at pH 3.5 ($H_3PO_4$) and UV detection at 200 nm. Quantification is done by external standardization.

In a preferred embodiment of a method of the invention, above 450 g, preferably above 500 g of dodecylguanidine or a salt or ester thereof, expressed per liter of the concentrate, were suspended.

In a preferred embodiment of a method of the invention at least 500 g/l of dodecylguanidine or a salt or ester thereof, expressed per liter of the concentrate, is suspended in the composition.

In a preferred embodiment of a method of the invention, the method is further comprising the step of adding a thickener to the suspension concentrate in an amount to obtain a viscosity between 500 and 1.000 mPa·s (cps), preferably around 750 mPa·s (cps).

The invention is further described by the following non-limiting examples which further illustrate the invention, and are not intended to, nor should they be interpreted to, limit the scope of the invention.

The present invention will be now described in more details, referring to examples that are not limitative.

It is supposed that the present invention is not restricted to any form of realization described previously and that some modifications can be added to the presented example of fabrication without reappraisal of the appended claims. For example, the present invention has been described referring to acetate of dodecylguanidine, but it is clear that the invention can be applied to salts of dodecylguanidine for instance or to mixtures of acetate of dodecylguanidine with other active ingredients.

EXAMPLES

Example 1: Preparation of Dodine 544 SC

Water was charged to a vessel. Formulation additives, in particular propylene glycol (antifreezing agent), ethoxylated alkylamine (wetting agent), acrylic graft polymer (dispersing agent), silicon oil (antifoaming agent), and 1,2-benzisothiazolin-3-one (preservative) were added according to the recipe presented in Table 1. The grounded active ingredient was suspended in the aqueous mixture. Hydroxyethylcellulose (thickener) was added until a viscosity of about 750 mPa·s (cps) was obtained, measured with a Brookfield system using spindle 2 at 20 rpm and 20° C. The particle size distribution of the mixture was measured using a particle analyzer. The data for Dodine 544 SC were as follows: mean 11.08 μm, standard deviation 9.015 μm, median 7.837 μm, variance 81.27 μm², C.V. 81.3%, Mode 5.354 μm, <10%: 2.634 μm, <25%:4.551 μm, <50%:7.837 μm, <75% 15.22 μm, <90% 24.09 μm.

TABLE 1

Dodine 544 SC

| Ingredients | Content (g/l at 20° C.) | Function |
|---|---|---|
| Dodine (technical, 98% purity) (Dodine, as pure) | 555.1 (544) | Active substance |
| Water | 383.9 | Solvent |
| Propylene glycol | 30.0 | Antifreeze |
| Ethoxylated Alkylamine | 30.0 | Wetting Agent |
| Acrylic graft polymer | 10.0 | Dispersing Agent |
| Silicon oil | 10.0 | Antifoaming agent |
| Hydroxyethylcellulose | 1.0 | Thickener |
| 1,2-Benzisothiazolin-3-one | 1.0 | Biocide |
| Total | 1021 g/l | |

Example 2: Storage Stability of Dodine 544 SC

An accelerated storage stability test, according to CIPAC method MT 46 was performed on samples obtained from the product described in Example 1. The results obtained for a set of parameters is listed in Table 2. As it can be seen from the results, the concentrated suspension concentrate according to an embodiment of the invention, remained stable.

Example 3: Efficacy Data for Dodine 544 SC

Short Description of the Experiment

Fungicides were applied with a mist blower from end of March 2010 to Mid June 2010. The set-up of the experiment was a randomised block design with 12 treatments and four replicates. Assessments were made according to EPPO-guidelines PP 1/152(3) Design and analysis of efficacy evaluation trials, PP 1/135(3) Phytotoxicity assessment, PP 1/181(3) Conduct and reporting of efficacy evaluation trials including GEP, PP 1/5(3) *Venturia inaequalis* and *V. pyrina*, CEB 14 Scabs of pears and apples; on shoot, fruit and leaf infections. The new fungicide formulations were compared to standards and a control treatment.

TABLE 2

Storage stability of the concentrated aqueous suspension obtained in Example 2.

| Test parameter | Initial sample | Sample stored 14 days at 54° C. |
|---|---|---|
| Appearance | | |
| physical state | liquid | liquid |
| opacity | opaque | opaque |
| color | white | white |
| pH | 5.97 | 5.94 |
| Viscosity (mPa · s (cps), 20° C.) | 810 | 820 |
| Persistent foaming (after 1 min - 1% -CIPC D - 30° C.) | <50 mL | <50 mL |
| d50-d90 | 8.94-29 | 10.8-34.9 |

TABLE 2-continued

Storage stability of the concentrated aqueous suspension obtained in Example 2.

| Test parameter | Initial sample | Sample stored 14 days at 54° C. |
|---|---|---|
| Wet sieve | | |
| retained on 315 µm | Not measured | Not measured |
| retained on 150 µm | 0.009% | 0.008% |
| retained on 40 µm | 0.290% | 0.307% |
| Active ingredient content | | |
| % w/w | 53.6 | 53.4 |
| g/l | 547.5 | 545.7 |

Orchard and Equipment

The experiment was conducted at trial site in Greece. The trial site is an orchard with cultivars of apple (Malus domestica, Pink lady variety). Treatments were applied with a mist blower, a ground speed of 0.18 kph. This resulted in a spray volume of 1000 l/ha.

Treatments

The following fungicides were applied:

| 1. | untreated | | |
|---|---|---|---|
| 2. | Dodine 544 SC | 0.125 l/100 l | 680 g active ingredient/ha |
| 3. | Syllit ® 400 SC | 0.170 l/100 l | 680 g active ingredient/ha |

Results

The preliminary results are presented in Table 3. In this means table, means followed by the same letter do not significantly differ (P=0.05, Student-Newman-Keuls). From the results it may be concluded that the Dodine 544 SC formulation controls scab on apples at least equally good and even better than Syllit® 400 SC.

TABLE 3

Field trial results

| | Part rate | | | | | |
|---|---|---|---|---|---|---|
| | Leaf 9 | Leaf 13 | Leaf 15 | Leaf 6 | Leaf 10 | Leaf 14 |
| | Rating type | | | | | |
| Treatment | Pest incidence | Pest incidence | Pest incidence | Pest severity | Pest severity | Pest severity |
| 1 | 0.00 c | 0.00 e | 100.00 a | 0.54 a | 4.49 a | 6.41 a |
| 2 | 100.00 a | 53.75 bcd | 92.50 ab | 0.00 b | 0.46 bc | 2.10 b |
| 3 | 100.00 a | 48.75 bcd | 88.75 ab | 0.00 b | 0.58 b | 2.08 b |

| | Part rate | | | | | |
|---|---|---|---|---|---|---|
| | Leaf 7 | Leaf 11 | Leaf 17 | Leaf 8 | Leaf 12 | Leaf 16 |
| | Rating type | | | | | |
| Treatment | Pest incidence | Pest incidence | Pest incidence | Pest severity | Pest severity | Pest severity |
| 1 | 51.25 a | 100.00 a | 0.00 c | 0.00 c | 0.00 d | 0.00 d |
| 2 | 0.00 b | 46.25 bcd | 7.50 bc | 100.00 a | 89.70 bc | 66.69 bc |
| 3 | 0.00 b | 51.25 bcd | 11.25 bc | 100.00 a | 87.43 bc | 67.24 bc |

Example 4

Figure 2:
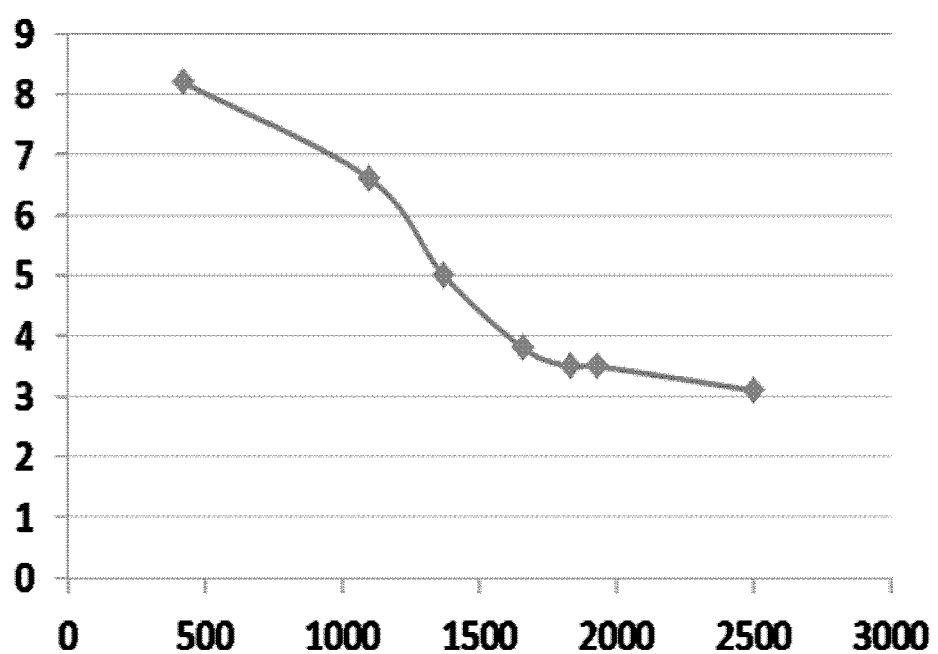
FIG. 2 provides a graphical representation of formulations wherein an average particle size is plotted against the viscosity of the formulation obtained.

Several dodine 600 SC formulations were prepared according to the compositions depicted in Table 4. The average particle size d50 (µm) is plotted in function of the viscosity of the composition, as displayed in FIG. 2. From FIG. 2 it can be seen that viscosity gradually increases from about 1500 mPa·s to above 3000 mPa·s for an average particle size of 4 and lower. Such a viscosity is undesirable as the formulation becomes too viscous, thus difficult to handle. Preferably, the viscosity of an SC formulation is comprised between 550 mPa·s and 1050 mPa·s, more preferably around 800 mPa·s. This value is obtained for an average particle size of 7 µm.

TABLE 4

Preparation of dodine 600 SC formulations

|  | g/l | g/l | g/l | g/10 l | weighed | % w/w |
|---|---|---|---|---|---|---|
| Water | 303.5 | 303.5 | 303.5 | 3035 | 3037.70 | 29.7 |
| Rhodorsil 454 AM | 10 | 10.0 | 10.0 | 100 | 100.00 | 1.0 |
| Tersperse 2500 | 10 | 10.0 | 10.0 | 100 | 100.00 | 1.0 |
| Dodine 96.5% | 635 | 635.0 | 635.0 | 6350 | 6376.30 | 62.4 |
| Rhodameen RAM7/PPG | 60 | 60.0 | 60.0 | 600 | 600.10 | 5.9 |
| Natrosol 250 HXR | 1 | 1.0 | 1.0 | 10 | / | |
| Promex Na2OS | 1.5 | 1.5 | 1.5 | 15 | / | |
|  | 1021.00 | 1021 | 1021 | 10210 | 10214.1 | 100.0 |

Example 5: Dodine 544 SC—Storage Stability, Pourability/Rinsability

A Dodine 544 SC formulation according to an embodiment of the invention was prepared. It contained around 54% w/w of dodine and 4% of a non-ionic wetting/dispersing agent.

Figure 3:
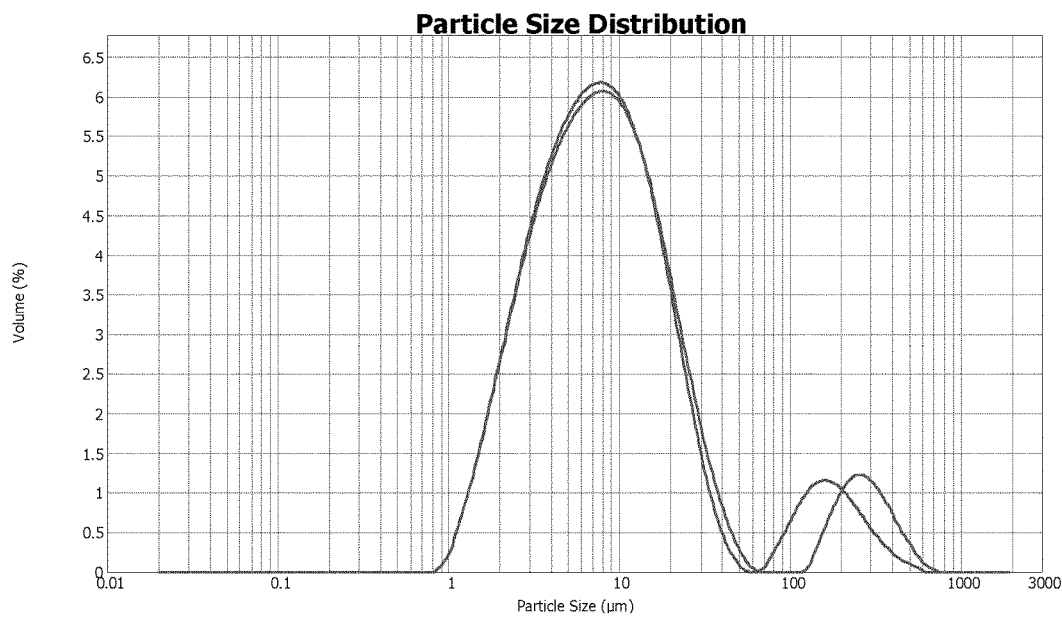
FIG. 3 depicts the particle size distribution of the Dodine 544 g/l SC formulation of Experiment 5, shortly after its preparation.
Figure 4:
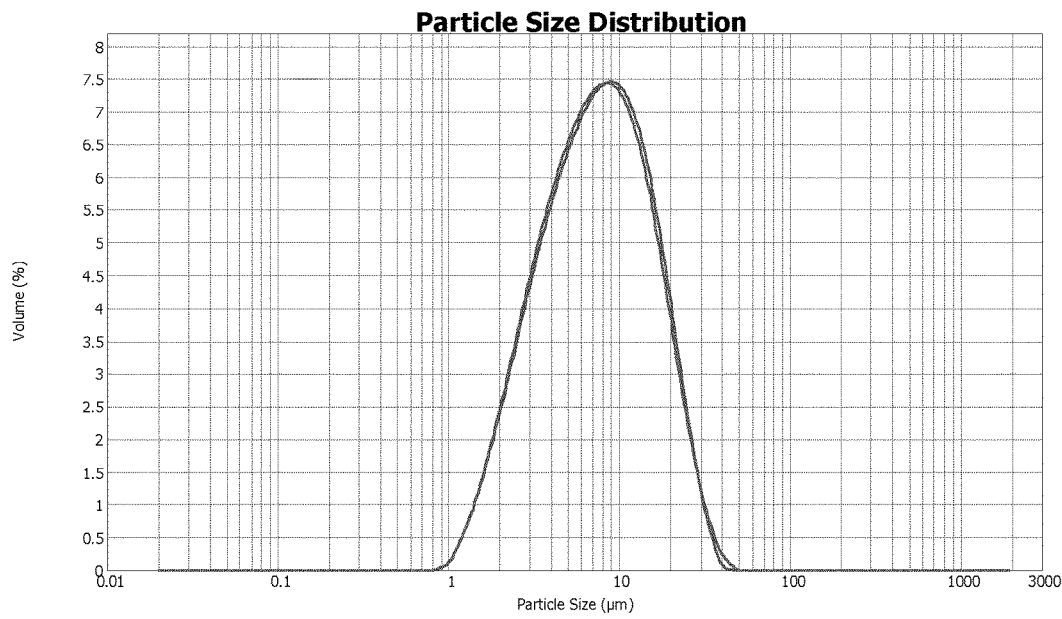
FIG. 4 depicts the particle size distribution of the Dodine 544 g/l SC formulation of Experiment 5, after storage for one year at 20° C.+/−2° C.

Its physico-chemical parameters were tested according to test methods known to a skilled person. The results are provided in Table 5. The particle size distribution is provided in FIGS. 3 and 4.

From the results it can be seen that the active ingredient content of samples measured after an accelerated storage stability test, wherein samples were stored for 14 days at 54° C., or after storage at ambient temperature for 1 year, remains stable. This indicates that no degradation has taken place.

TABLE 5

Storage stability of the concentrated aqueous suspensions of Example 5.

| Test parameter | Initial sample | Sample stored 14 days at 54° C. (CIPAC MT 46.3.1). | Storage stability 1 year (Croplife N° 17) |
|---|---|---|---|
| Active ingredient content | | | |
| % w/w | 53.58 +/− 0.20 | 53.58 +/− 0.62 | 54.20 +/− 0.87 |
| g/l | 551.2 +/− 2.0 | 551.1 +/− 6.5 | 557.6 +/− 8.9 |
| Appearance (visual) | | | |
| physical state | liquid | liquid | liquid |
| opacity | opaque | opaque | opaque |
| color | white | white | white |
| d50 | 7.940 μm | 9.663 μm | 7.434 μm |
| Wet sieve test | | | |
| (material retained on a 75 μm test sieve, CIPAC MT 185) | 0.076% w/w | 0.241% w/w | 0.060% w/w |
| Pourability - rinsability (CIPAC MT 148) | | | |
| Pour residue | 3.29% | 3.52% | |
| Rinsed residue | 0.12% | 0.16% | |

From the results of the wet sieve test and pourability/rinsability test it becomes clear that although particles of above average size are present compared to prior art dodine formulations, stability is maintained even up to one year. This is underlined by the values which show practically now change over this long period of time. As can be seen from the accelerated storage stability data, stability was not compromised by an increase in particle size from 7.9 μm initially to 9.7 μm after 14 days at 54° C.+/−2° C. in a closed glass bottle test according to CIPAC MT 46.3.1.

This stability of the highly concentrated dodine formulation was also observed after 7 days at 0° C.+/−2° C. in a closed glass bottle test according to CIPAC MT 46.3.

Example 6: Dodine 600 SC—Particle Size, Viscosity, Storage Stability

Several dodine 600 SC formulations were prepared, as presented in Table 6. They differed by the size of the particles of the dodine active ingredient. These were obtained using a conventional grinder. The average particle size varied between 2 and 27 μm, as measured using laser diffraction. The viscosity of the formulations obtained was measured using a Brookfield viscosity meter, a spindle 20, 20 rotations per minute, and a temperature of 20° C.

Figure 5:
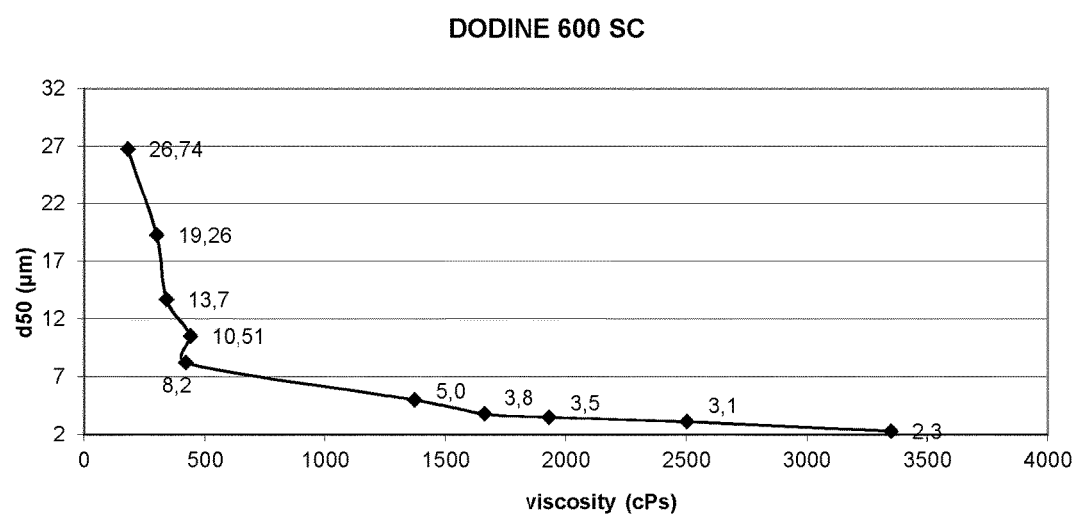
FIG. 5 depicts the viscosity of several Dodine 600 SC formulations with varying d50 particle size.

The results of the viscosity measurements were plotted against the average particle size of the dodine active ingredient in the formulation, as depicted in FIG. 5. As can be seen from this figure, the viscosity was high for particles below 5 μm, in particular 1370-3350 cPs. Unexpectedly, the viscosity drastically improved for higher particle sizes. The data points depicted showed a viscosity of 420-180 cPs for a particle size varied from 8.2 μm to 26.74 μm, as detailed in Table 6.

Sample fractions of the 600 SC formulations were stored for 14 days at 54° C. This represents an accelerated storage stability test. An assessment was conducted concerning their appearance to conclude on the products storage stability. The results are summarized in Table 7.

Upon visual inspection of the samples a liquid with a clear layer on the top was observed. This layer varied from 1% to 38% with the d50 particle size increasing from 3.2 μm to 26.74 μm. For the sample with lowest particle size of 3.2 μm, no sediment was observed on the bottom of the sample recipient. For the samples of d50 between 3.5 and 19.26 μm a small amount of sediment was observed on the bottom.

However, the sample became homogeneous after shaking. For the sample with d50 of 26.4 μm, hard sediment was observed on the bottom which could not be homogenized with shaking. Claying of the particle sediment occurred.

We conclude from this experiment that for a Dodine 600 SC formulation, a formulation with a d50 particle size lower than 5 μm had a viscosity above about 1500 cPs, which was difficult to handle. The increase of the particle size of dodine above 5 μm led to a workable viscosity. The formulation with a d50 particle size higher than 20 μm was not stable. Too hard sediment (caking) appeared. Sediment formation was not reversible.

Highly concentrated formulations with a dodine d50 particle size above 5 μm and below 20 μm provided storage stable products with workable viscosity.

TABLE 6

Particle size and viscosity of freshly prepared dodine 600 SC formulations

| d50 (μm) | Viscosity (cPs) |
|---|---|
| 180 | 26.74 |
| 300 | 19.26 |
| 340 | 13.7 |
| 440 | 10.51 |
| 420 | 8.2 |
| 1370 | 5.0 |
| 1660 | 3.8 |
| 1930 | 3.5 |
| 2500 | 3.1 |
| 3350 | 2.3 |

TABLE 7

Particle size and visual appearance after an accelerated storage stability test of 14 days at 54° C.

| d50 (um) | Appearance |
|---|---|
| 26.74 | Liquid with 38% of a clear layer on the top and a hard sediment on the bottom (claying). Non-homogeneous after shaking |
| 19.26 | Liquid with 10% of a clear layer on the top and a small sediment on the bottom (claying). Homogeneous after shaking |
| 13.7 | Liquid with 5% of a clear layer on the top and a small sediment on the bottom (claying). Homogeneous after shaking |
| 10.51 | Liquid with 2% of a clear layer on the top and a small sediment on the bottom (claying). Homogeneous after shaking |
| 8.2 | Liquid with 2% of a clear layer on the top and a small sediment on the bottom (claying). Homogeneous after shaking |
| 4.62 | Liquid with 1% of a clear layer on the top and a small sediment on the bottom (claying). Homogeneous after shaking |
| 3.9 | Liquid with 1% of a clear layer on the top and a small sediment on the bottom (claying). Homogeneous after shaking |
| 3.5 | Liquid with 1% of a clear layer on the top and a small sediment on the bottom (claying). Homogeneous after shaking |
| 3.2 | Liquid with 1% of a clear layer on the top and no sediment on the bottom (claying). |

What is claimed is:

1. A suspension concentrate composition exhibiting long-term storage stability, the composition consisting of:
    a) at least 400 g of dodine particles/l, and expressed by weight based on the total weight of the composition;
    b) 0 to 10% by weight of an anti-freeze compound;
    c) 1 to 10% by weight of a wetting agent;
    d) 0 to 2% by weight of a dispersing agent;
    e) 0 to 5% by weight of an antifoaming agent;
    f) 30 to 45% by weight water;
wherein:
    the median diameter of the dodine particles ($d_{50}$) is 7-20 μm,
    the wetting agent is selected from the group consisting of alkylamine ethoxylates, acrylate graft copolymers, alkylphenol ethoxylates, alcohol ethoxylates, and tristyrylphenol ethoxylates;
    the suspension concentrate has a viscosity between 550 and 1,000 mPa-s, as measured with a Brookfield viscosity meter using a spindle 2, 20 rpm and 20° C., and
    wherein the suspension concentrate composition, prior to dilution, remains stable upon storage such that the dodine particles do not settle out of the suspension concentrate for a period of at least 12 months.

2. A suspension concentrate composition exhibiting long-term storage stability, the composition consisting of:
    a) at least 400 g of dodine particles/l, and expressed by weight based on the total weight of the composition;
    b) 0 to 10% by weight of an anti-freeze compound;
    c) 1 to 10% by weight of a wetting agent selected from the group consisting of alkylphenol ethoxylates and tristyrylphenol ethoxylates;
    d) 1 to 2% by weight of a dispersing agent, the dispersing agent comprising an acrylate graft copolymer;
    e) 0 to 5% by weight of an antifoaming agent;
    e) 30 to 45% by weight water,
    wherein the median diameter of the dodine particles (d50) is 7-20 μm;
    the suspension concentrate has a viscosity between 550 and 1,000 mPa-s, as measured with a Brookfield viscosity meter using a spindle 2, 20 rpm and 20° C.; and
    wherein the suspension concentrate composition, prior to dilution, remains stable upon storage such that the dodine particles do not settle out of the suspension concentrate for a period of at least 12 months.

* * * * *